United States Patent
Rempfler

Patent Number: 5,399,545
Date of Patent: Mar. 21, 1995

[54] SUBSTITUTED BENZYL CARBAMATES WITH HERBICIAL PROPERTIES

[75] Inventor: Hermann Rempfler, Ettingen, Switzerland

[73] Assignee: Ciba-Geigy Corporation, Ardsley, N.Y.

[21] Appl. No.: 142,263

[22] Filed: Oct. 22, 1993

[30] Foreign Application Priority Data

Nov. 5, 1992 [CH] Switzerland ............. 3431/92

[51] Int. Cl.⁶ .............. A01N 43/30; C07D 317/46
[52] U.S. Cl. .............................. 504/296; 549/438
[58] Field of Search ................. 549/438; 504/296

[56] References Cited

U.S. PATENT DOCUMENTS

| | | | |
|---|---|---|---|
| 4,666,502 | 5/1987 | Seckinger et al. | 549/448 |
| 4,722,935 | 2/1988 | Ehrenfreund | 514/465 |
| 4,859,783 | 8/1989 | Ehrenfreund | 549/439 |
| 5,078,783 | 1/1992 | Baker | 71/105 |
| 5,099,059 | 3/1992 | Baker | 560/24 |
| 5,194,661 | 3/1993 | Baker | 504/303 |

FOREIGN PATENT DOCUMENTS 0480902  4/1992  European Pat. Off.

*Primary Examiner*—Nicky Chan
*Attorney, Agent, or Firm*—Marla J. Mathias; George R. Dohmann

[57] ABSTRACT

Substituted benzyl carbamates of formula I

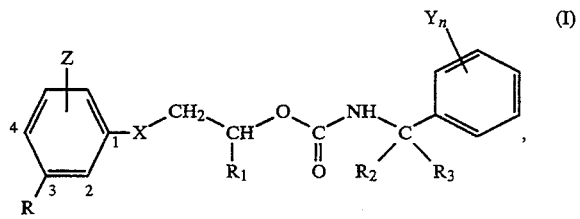

wherein
R is halogen, trifluoromethyl, cyano, nitro or $C_1$-$C_3$-haloalkoxy;
Z is hydrogen or halogen; or
Z and R together in 2- and 3-position of the phenyl ring form the group —$OCF_2O$—;
$R_1$ is $C_1$-$C_5$alkyl; wherein in case R and Z together in 2- and 3-position of the phenyl ring form the group —$OCF_2$—,
$R_2$ and $R_3$ are each independently of the other hydrogen, methyl or ethyl; and in case R is halogen, trifluoromethyl, cyano, nitro or $C_1$-$C_3$haloalkoxy, $R_2$ is methyl or ethyl; and $R_3$ is hydrogen, methyl or ethyl;
X is oxygen, sulfur, —SO— or —$SO_2$—;
Y is hydrogen, halogen, $C_1$-$C_3$alkyl, $C_1$-$C_3$haloalkyl, $C_1$-$C_3$alkoxy or cyano; and
n is 0, 1 or 2;

and the diastereoisomers thereof, have pre- and post-emergence herbicidal properties. The preparation of these compounds and the use thereof as herbicides are described.

15 Claims, No Drawings

SUBSTITUTED BENZYL CARBAMATES WITH HERBICIDAL PROPERTIES

The present invention relates to novel herbicidally active substituted benzyl carbamates, to their preparation, to compositions containing said benzyl carbamates as active ingredient, and to the use thereof for controlling weeds, especially in crops of useful plants such as cereals, rice, maize, soybeans and cotton.

Substituted alkyl and phenyl carbamates with herbicidal properties are already known and disclosed, inter alia, in U.S. Pat. Nos. 5,078,783 and 5,099,059.

There have now been found novel substituted benzyl carbamates with herbicidal properties and having good activity.

The novel benzyl carbamates have the formula I

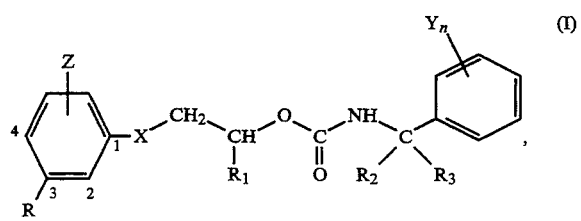

wherein
R is halogen, trifluoromethyl, cyano, nitro or $C_1$–$C_3$-haloalkoxy;
Z is hydrogen or halogen; or
Z and R together in 2- and 3-position of the phenyl ring form the group —$OCF_2O$—;
$R_1$ is $C_1$–$C_5$alkyl; wherein in case
R and Z together in 2- or 3-position of the phenyl ring form the group —$OCF_2O$—,
$R_2$ and $R_3$ are each independently of the other hydrogen, methyl or ethyl; and in case R is halogen, trifluoromethyl, cyano, nitro or $C_1$–$C_3$haloalkoxy, $R_2$ is methyl or ethyl; and $R_3$ is hydrogen, methyl or ethyl;
X is oxygen, sulfur, —SO— or —$SO_2$—;
Y is hydrogen, halogen, $C_1$–$C_3$alkyl, $C_1$–$C_3$haloalkyl, $C_1$–$C_3$alkoxy or cyano; and
n is 0, 1 or 2;
and the diastereoisomers thereof.

Halogen in the above definitions will be taken to mean iodo and, preferably, fluoro, chloro and bromo.

Alkyl groups may suitably be straight-chain or branched alkyl groups, typically methyl, ethyl, n-propyl, isopropyl, n-butyl, sec-butyl, isobutyl, tert-butyl, n-pentyl and the isomers thereof. Methyl and ethyl are preferred.

Haloalkyl may suitably be alkyl substituted by one or more than one halogen atom, preferably by one to three halogen atoms, the halogen being bromo or iodo and, preferably, fluoro or chloro. Illustrative examples are fluoromethyl, difluoromethyl, chloromethyl, dichloromethyl, trichloromethyl and, preferably, trifluoromethyl.

Alkoxy may suitably be methoxy, ethoxy, n-propoxy and isopropoxy.

Haloalkoxy may suitably be difluoromethoxy, trifluoromethoxy, 2,2,2-trifluoroethoxy and 1,1,2,2-tetrafluoroethoxy. Difluoromethoxy and trifluoromethoxy are preferred.

When applied postemergence, but especially preemergence, the novel benzyl carbamates of formula I have good selectivity in crops of useful plants such as cereals, rice, maize, soybeans and cotton.

Compounds of formula I, wherein R is chloro, bromo, trifluoromethyl or trifluoromethoxy, are preferred.

Those compounds of formula I are also preferred wherein Z is hydrogen or fluoro.

Preferred compounds of formula I also include those wherein $R_1$ is methyl or ethyl.

Compounds of formula I, wherein $R_2$ and $R_3$ are each independently of the other hydrogen or methyl, are also suitable.

Further preferred compounds of formula I are also those wherein X is oxygen or sulfur.

Important compounds of formula I are those wherein Y is hydrogen, fluoro, chloro, methyl, trifluoromethyl, methoxy or cyano.

Particularly important compounds of formula I are those wherein R is trifluoromethyl; Z is hydrogen; $R_1$ is ethyl; $R_2$ is methyl or ethyl; $R_3$ is hydrogen; X is oxygen; Y is fluoro, chloro, methyl, trifluoromethyl, methoxy or cyano; and n is 0 or 1.

Particularly important compounds of formula I are also those wherein Z and R together in 2- and 3-position of the phenyl ring form a group —$OCF_2O$—; $R_1$ is ethyl; $R_2$ and $R_3$ are hydrogen; X is oxygen; Y is fluoro, chloro, methyl, trifluoromethyl, methoxy or cyano; and n is 0 or 1.

Compounds of formula I are also particularly preferred wherein Z and R together in 2- and 3-position of the phenyl ring form a group —$OCF_2O$—; $R_1$ is $C_1$–$C_5$alkyl; $R_2$ and $R_3$ are each independently of the other hydrogen, methyl or ethyl; X is oxygen, sulfur, —SO— or —$SO_2$—; and Y is fluoro, chloro, methyl, trifluoromethyl, methoxy or cyano.

Among these compounds, those compounds of formula I are of particular importance wherein Z and R together in 2- and 3-position of the phenyl ring form a group —$OCF_2O$—; $R_1$ is methyl or ethyl; $R_2$ is hydrogen or methyl; $R_3$ is hydrogen; X is oxygen; and Y is fluoro, chloro, methyl or methoxy.

Particularly preferred compounds of formula I are those wherein R is chloro, bromo, trifluoromethyl, difluoromethoxy, trifluoromethoxy, cyano or nitro; Z is hydrogen or, in 2- or 4-position, is fluoro; $R_1$ is $C_1$–$C_5$alkyl; $R_2$ is methyl or ethyl; $R_3$ is hydrogen, methyl or ethyl; X is oxygen, sulfur, —SO— or —$SO_2$—; and Y is fluoro, chloro, methyl, trifluoromethyl, methoxy or cyano.

Among these compounds, those compounds of formula I are of particular importance wherein R is trifluoromethyl or cyano; Z is hydrogen; $R_1$ is methyl or ethyl; $R_2$ is methyl; $R_3$ is hydrogen; X is oxygen; and Y is fluoro, chloro, methyl or methoxy.

Particularly preferred compounds are those of formulae Ia and Ib

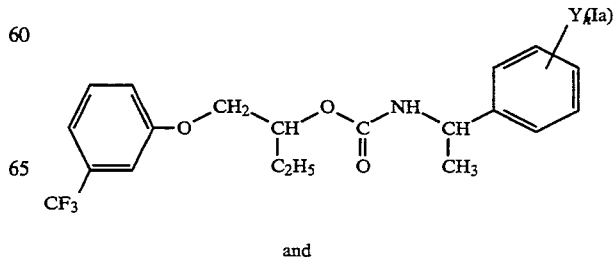

and

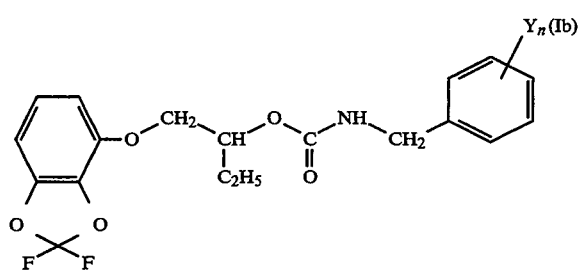

wherein Y and n are as defined for formula I.

Among these compounds, those compounds of formulae Ia and Ib are of very particular importance wherein Y is fluoro, chloro, methyl or methoxy; and n is 0, 1 or 2.

The novel process for the preparation of the compounds of formula I is carried out in general accordance with known procedures and comprises a) to prepare the benzyl carbamate derivatives of formula I, reacting a compound of formula II

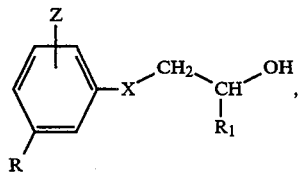 (II)

wherein R, Z, $R_1$ and X are as defined for formula I, with a benzyl isocyanate of formula III

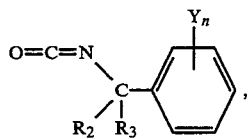 (III)

wherein $R_2$, $R_3$, Y and n are as defined for formula I, in the absence or presence of a catalyst and in an inert organic solvent; or b) first chloroformylating a compound of formula II

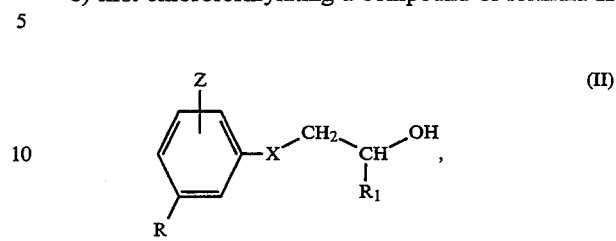 (II)

under customary conditions, preferably with phosgene or diphosgene, to a compound of formula IV

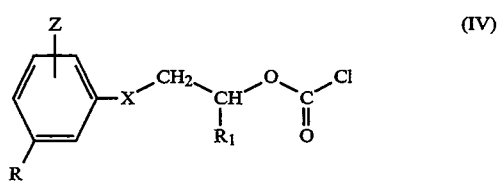 (IV)

in which formulae II and IV the substituents R, Z, $R_1$ and X are as defined for formula I, and subsequently reacting this intermediate with a benzylamine of formula V

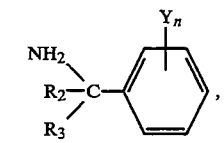 (V)

wherein $R_2$, $R_3$, Y and n are as defined for formula I, in an inert organic solvent and in the presence of an acid scavenger such as a tertiary amine or pyridine.

Process variants a) and b) are carried out in accordance with reaction scheme 1.

Reaction scheme 1:

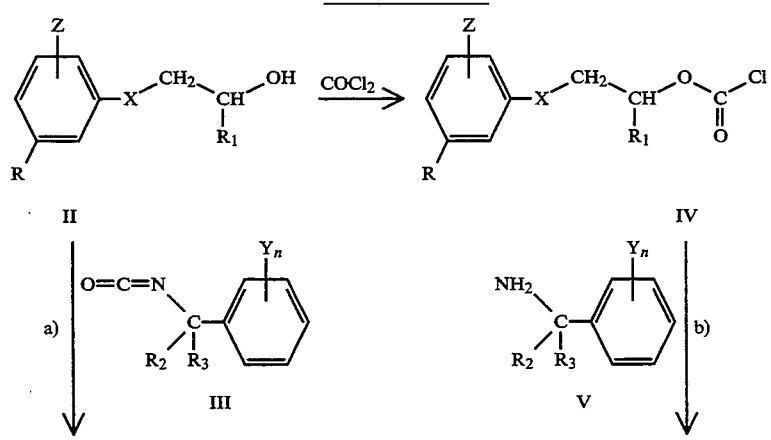

Reaction scheme 1:

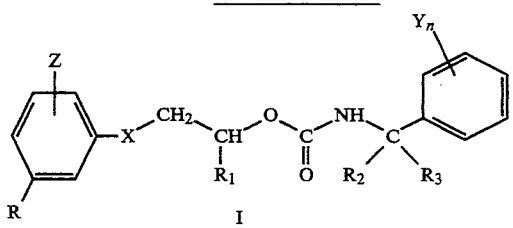

The addition reaction of process variant a) may conveniently be carried out by reacting the alcohol of formula II and the benzyl isocyanate of formula III in an inert aprotic organic solvent, typically an aliphatic or cyclic ether such as diethyl ether, 1,2-dimethoxyethane, tetrahydrofuran or dioxane, or in a chlorinated aliphatic hydrocarbon such as methylene chloride, or in an aromatic hydrocarbon such as toluene or xylene, or in an aliphatic ester such as ethyl acetate, in the presence of a catalyst, conveniently 4-N,N-dimethylaminopyridine, triethylamine and/or dibutyltin dilaurate, preferably in the temperature range from 20° C. to the reflux temperature of the reaction solution.

In process variant b), the chloroformate of formula IV is reacted with the benzylamine of formula V conveniently in an inert aprotic organic solvent in the presence of an organic base, as described in process variant a), in the temperature range from −20° to +40° C., preferably from +5° to 20° C. During working up, the reaction mixture obtained is preferably washed with water and dilute acid in order to separate amine by-products as salts.

The alcohols of formula II (IIa: $X_1$ = —O— or —S—; IIb; and IIc) can be prepared by standard procedures described in the literature (e.g. U.S. Pat. No. 5,099,059), conveniently in accordance with the following reaction scheme 2.

Reaction scheme 2:

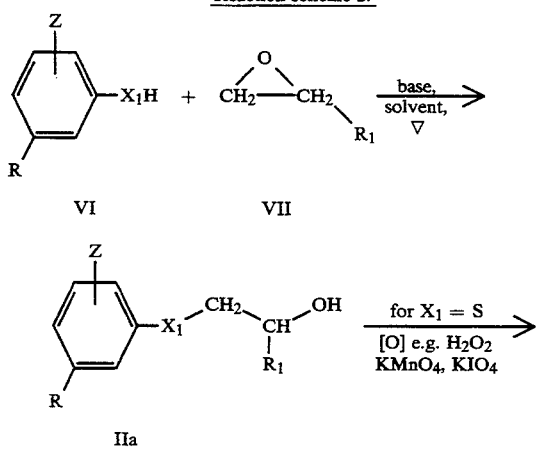

-continued
Reaction scheme 2:

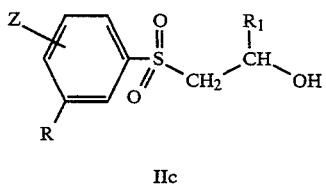

In this reaction, the compounds of formulae IIa, IIb and IIc are obtained by reacting the (thio)phenol derivative of formula VI, wherein R and Z have the given meanings and $X_1$ is oxygen or sulfur, with an epoxide of formula VII, wherein $R_1$ has the given meaning, in water or N,N-dimethylformamide and in the presence of a basic catalyst, preferably at reflux temperature. An excess of epoxide may be used to achieve complete reaction with the (thio)phenol. Potassium hydroxide (10% molar) is conveniently used as basic catalyst. The reaction mixture is washed with aqueous base to remove unreacted thio(phenol), dried over a drying agent, and concentrated to remove excess epoxide.

The oxidation of the thiophenoxy alcohol of formula IIa, wherein Z, R and $R_1$ have the given meanings and $X_1$ is sulfur, is carried out by conventional methods, conveniently in an inert organic solvent such as methylene chloride, typically using hydrogen peroxide, potassium permanganate or potassium iodate as oxidising agent. Depending on the type and stoichiometric amount of the oxidising agent, the product of formula IIb (sulfoxide) or IIc (sulfone) is obtained.

The preparation of the chloroformate derivatives of formula IV is carried out by per se known methods (e.g. U.S. Pat. No. 5,099,059), conveniently in an inert organic solvent such as toluene or methylene chloride, and with an excess of phosgene or diphosgene in the presence of a catalytic amount of N,N-dimethylformamide, preferably in the temperature range from 20° to 80° C.

The preparation of the intermediate of formula IIa can also be carried out in the presence of lithium hydroxide monohydrate and in the absence of a solvent, under pressure, in accordance with reaction scheme 3.

Reaction scheme 3:

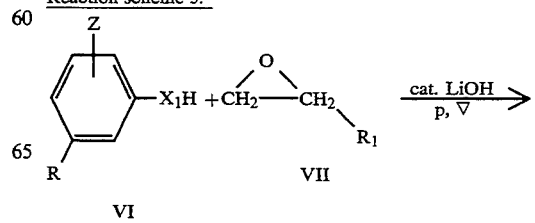

Reaction scheme 3:

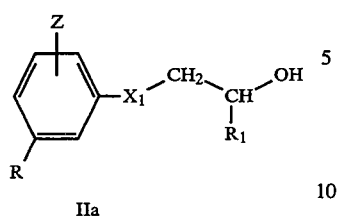

IIa

Reaction scheme 4:

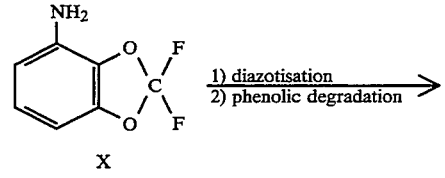

X

VIa

In this reaction, a (thio)phenol derivative of formula VI, wherein R and Z are as defined for formula I and $X_1$ is oxygen or sulfur, is heated together with an epoxide of formula VII, wherein $R_1$ is as defined for formula I, in the presence of a catalytic amount of lithium hydroxide monohydrate and in the absence of a solvent, under pressure (pressure vessel, bomb tube), for 1 to 24 hours, preferably for 8 to 16 hours, to 80°–180° C., preferably 100°–160° C. After cooling the reaction mixture, the desired product of formula IIa is obtained in quantitative yield and high purity after conventional working up.

This process is novel and has been specially developed for the synthesis of the compounds of formula I. It is simple, affords the products in almost quantitative yield and high purity, and is therefore also advantageous from the ecological aspect. This process likewise constitutes an object of the invention.

The compounds of formulae I, IIa, IIb, IIc and IV can be isolated and purified in per se known manner. Those skilled in the art will be familiar with the order in which certain reactions described in process variants a) and b) are conveniently carried out in order to avoid possible side-reactions.

Provided no planned synthesis for isolating pure isomers is carried out, the product is obtained as a mixture of two or more isomers. The isomers can be separated by per se known methods.

The intermediates of formula IId

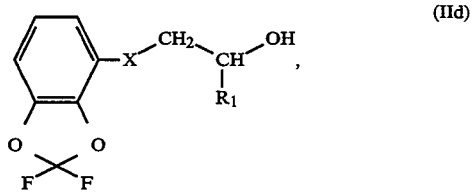

(IId)

wherein $R_1$ and X are as defined for formula I, are novel and have been specially developed for the synthesis of the compounds of formula I. They therefore likewise constitute an object of the present invention.

The same preferences as have been indicated in connection with the compounds of formula I also apply to the intermediates of formulae II and IV.

The starting compounds of formulae III, V, VI and VII required for the syntheses are either known or can be prepared by different processes known from the literature, conveniently for compounds of formula VIa according to reaction scheme 4.

The preparation of the required starting compound of formula X is described in EP-A-0 198 797.

The formulations, i.e. the compositions, preparations or mixtures containing the compound of formula I and, where appropriate, one or more than one solid or liquid adjuvant, are prepared in known manner, e.g. by homogeneously mixing and/or grinding the herbicidal compounds with extenders, e.g. solvents, solid carriers and, in some cases, surface-active compounds (surfactants).

Suitable solvents are: aromatic hydrocarbons, preferably the fractions containing 8 to 12 carbon atoms such as mixtures of alkylbenzenes, typically xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters such as propylene glycol or dipropylene glycol ether; ketones such as cyclohexanone, isophorone or diacetone alcohol; strongly polar solvents such as N-methyl-2-pyrrolidone, dimethyl sulfoxide or water; vegetable oils and their esters such as rapeseed oil, castor oil or soybean oil; or also in some cases silicone oils.

The solid carriers used typically for dusts and dispersible powders are normally natural mineral fillers such as calcite, talcum, kaolin, montmorillonite or attapulgite. To enhance the physical properties it is also possible to add highly dispersed silicic acid or highly dispersed absorbent polymers. Suitable granulated adsorptive carriers are porous types, conveniently pumice, broken brick, sepiolite or bentonite; and suitable nonsorbent carriers are materials such as calcite or sand. In addition, innumerable pregranulated materials of inorganic or organic nature can be used, especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), typically the sodium or potassium salts of oleic or stearic acid, or of natural fatty acid mixtures which can be obtained, inter alia from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, typically salts of the phosphated polyadduct of p-nonylphenol with 4 to 14 mol of ethylene oxide, or phospholipids.

Nonionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable nonionic surfactants.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications:

"McCutcheon's Detergents and Emulsifiers Annual", McPublishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Handbook of Surfactants), Carl Hanser Verlag, Munich-/Vienna 1981.

The herbicidal compositions usually contain 0.1 to 99% by weight, preferably 0.1 to 95% by weight, of a compound of formula I, 1 to 99% by weight of a solid or liquid adjuvant, and 0 to 25% by weight, preferably 0.1 to 25% by weight, of a surfactant.

Whereas commercial products will preferably be formulated as concentrates, the end user will normally use dilute formulations.

The compositions may also contain further ingredients such as stabilisers, typically vegetable oils or epoxidised vegetable oils (epoxidised coconut oil, rapeseed oil or soybean oil), antifoams such as silicone oil, preservatives, viscosity regulators, binders, tackifiers as well as fertilisers or other chemical agents to obtain special effects.

In particular, preferred formulations are made up as follows (throughout, percentages are by weight):

| Emulsifiable concentrates: | |
| --- | --- |
| herbicide: | 1 to 90%, preferably 5 to 50% |
| surfactant: | 5 to 30%, preferably 10 to 20% |
| liquid carrier: | 15 to 94%, preferably 70 to 85% |
| Dusts: | |
| herbicide: | 0.1 to 10%, preferably 0.1 to 1% |
| solid carrier: | 99.9 to 90%, preferably 99.9 to 99% |
| Suspension concentrate: | |
| herbicide: | 5 to 75%, preferably 10 to 50% |
| water | 94 to 24%, preferably 88 to 30% |
| surfactant: | 1 to 40%, preferably 2 to 30% |
| Wettable powder: | |
| herbicide: | 0.5 to 90%, preferably 1 to 80% |
| surfactant: | 0.5 to 20%, preferably 1 to 15% |
| solid carrier: | 5 to 95%, preferably 15 to 90% |
| Granulate: | |
| herbicide | 0.5 to 30%, preferably 3 to 15% |
| solid carrier: | 99.5 to 70%, preferably 97 to 85% |

A. Formulation Examples for compounds of formula I (throughout, percentages are by weight)

| 1. Wettable powder | a) | b) | c) |
| --- | --- | --- | --- |
| compound of Table 1 | 20% | 50% | 0.5% |
| Na ligninsulfonate | 5% | 5% | 5% |
| Na laurylsulfate | 3% | — | — |
| Na diisobutylnaphthalene-sulfonate | — | 6% | 6% |
| octylphenol polyethylene glycol ether (7–8 mol EO) | — | 2% | 2% |
| highly dispersed silica | 5% | 27% | 27% |
| kaolin | 67% | — | — |
| sodium chloride | — | — | 59.5% |

The herbicide is thoroughly mixed with the adjuvants and the mixture is thoroughly ground in a suitable mill to give a wettable powders which can be diluted with water to give suspensions of any desired concentration.

| 2. Emulsifiable Concentrates | a) | b) |
| --- | --- | --- |
| compound of Table 1 | 10% | 1% |
| Ca dodecylbenzenesulfonate | 3% | 3% |
| octylphenol polyethylene glycol ether (4–5 Mol EO) | 3% | 3% |
| castor oil polyethylene glycol ether (36 mol EO) | 4% | 4% |
| cyclohexanone | 30% | 10% |
| xylene mixture | 50% | 79% |

Emulsions of any desired concentration can be prepared from such concentrates by dilution with water.

| 3. Dusts | a) | b) |
| --- | --- | --- |
| compound of Table 1 | 0.1% | 1% |
| talcum | 99.9% | — |
| kaolin | — | 99% |

Ready for use dusts are obtained by intimately mixing the carriers with the herbicide.

| 4. Extruder granulate | a) | b) |
| --- | --- | --- |
| compound of Table 1 | 10% | 1% |
| Na ligninsulfonate | 2% | 2% |
| carboxymethyl cellulose | 1% | 1% |
| kaolin | 87% | 96% |

The herbicide is mixed with the adjuvants, the mixture is ground and moistened with water. This mixture is extruded and subsequently dried in a stream of air.

| 5. Coated granulate | |
| --- | --- |
| compound of Table 1 | 3% |
| polyethylene glycol (MG200) | 3% |
| kaolin | 94% |

The finely ground herbicide is uniformly applied to the kaolin moistened with polyethylene glycol in a mixer to give a non-dusting coated granulate.

| 6. Suspension concentrate | a) | b) |
| --- | --- | --- |
| compound of Table 1 | 5% | 40% |
| ethylene glycol | 10% | 10% |
| nonylphenol polyethylene glycol ether (15 mol EO) | 1% | 6% |
| Na ligninsulfonate | 5% | 10% |
| carboxymethyl cellulose | 1% | 1% |
| 37% aqueous solution of formaldehyde | 0.2% | 0.2% |
| silicone oil in the form of a 75% aqueous emulsion | 0.8% | 0.8% |
| water | 77% | 32% |

The finely ground herbicide is intimately mixed with the adjuvants to give a suspension concentrate from which suspensions of any desired concentration can be prepared by dilution with water.

| 7. Salt solution | |
| --- | --- |
| compound of Table 1 | 5% |
| isopropylamine | 1% |
| octylphenol polyethylene glycol ether (78 mol EO) | 91% |

The compounds of formula I are used in unmodified form, e.g. as obtainable direct from the synthesis or preferably as compositions together with the standard auxiliaries of formulation technology and are·therefore processed in known manner to emulsifiable concentrates, directly sprayable or dilutable solutions, dilute emulsions, wettable powders, soluble powders, dusts, granular formulations, and also encapsulations in e.g. polymeric substances. The methods of application, typically spraying, atomising, dusting, scattering or pouting, are chosen in accordance with the intended objectives and the prevailing circumstances. The rates of application are usually from 0.005 to 2 kg per hectare, preferably from 0.01 to 1 kg per hectare.

B. Working Examples

Example P1 1-(3-Trifluoromethylphenoxy)-2-butanol (intermediate)

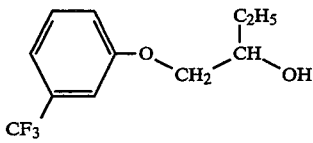

40.5 g of 3-hydroxybenzotrifluoride, 18.0 g of α-butylene oxide and 1.0 g of lithium hydroxide monohydrate are heated in a bomb tube (pressure reactor) for 16 hours to 140° C. After cooling the reactor, the reaction mixture is dissolved in 200 ml of ethyl acetate and the organic phase is washed with water and then dried over sodium sulfate and concentrated. The desired product, 1-(3-trifluoromethylphenoxy)-2-butanol, is obtained in a yield of 54.0 g and in high purity. The product can be used in the subsequent reaction without further purification.

Example P2 1-(3-Chlorophenoxy)-2-butanol (intermediate) is obtained in accordance with the general procedure described in Example P1 as an oil by using 51.4 g of 3-chlorophenol, 28.8 g of α-butylene oxide and 1.0 g of lithium hydroxide monohydrate. Yield: 71.4 g; b.p. 83°–84° C./0.04 torr.

EXAMPLE P3 1-(3-Cyanophenoxy)-2-butanol (intermediate) is obtained in accordance with the general procedure described in Example P1 as an oil by using 20.7 g of 3-cyanophenol, 13.8 g of α-butylene oxide and 0.5 g of lithium hydroxide monohydrate. Yield: 25.9 g; b.p. 116°–118° C./0.04 torr.

EXAMPLE P4 O—(3-Trifluoromethylphenoxy)-2-butylchloroformate (intermediate)

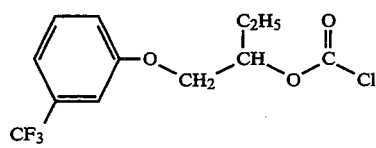

46.8 g of 1-(3-trifluoromethylphenoxy)butan-2-ol in 200 ml of toluene are added to 125 ml of a 1.93 molar solution of phosgene in toluene and 0.5 ml of N,N-dimethylformamide. When the slightly exothermic reaction has subsided, the reaction mixture is heated for 8 hours to 60° C. The reaction mixture is then concentrated to give the desired product, O—(3-trifluoromethylphenoxy)-2-butylchloroformate, in quantitative yield. The product can be used in the subsequent reaction without further purification.

Example P5 —O—[1-(3-Trifluoromethylphenoxy)-2-butylp9 -N-(2-methylbenzyl)carbamate

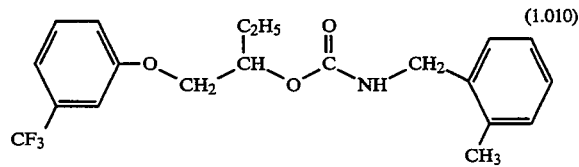

(1.010)

2.2 g of O—(3-trifluoromethylphenoxy)-2-butylchloroformate in 20 ml of methylene chloride are cooled to 5° C. With stirring, a solution of 0.9 g of 2-methylbenzylamine and 0.75 g of triethylamine in 20 ml of methylene chloride is then added dropwise. When the exothermic reaction has subsided, the mixture is allowed to stand for 2 hours at 22° C. and then 20 ml of 1N hydrochloric acid are added. The organic phase is separated, dried over sodium sulfate and concentrated. The residual yellow oil is chromatographed on silica gel with ethyl acetate/hexane ⅓ as eluant, giving 1.8 g of the desired product, O—[1-(3-trifluoromethylphenoxy)-2-butyl]-N-(2-methylbenzyl)carbamate, with a melting point of 61°–63° C.

EXAMPLE P6 O—[1-(3-Trifluoromethylphenoxy)-2-butyl]-N-benzylcarbamate

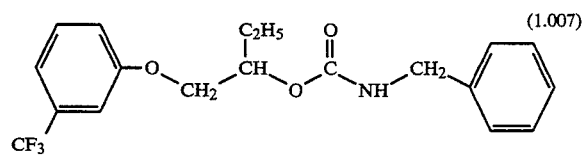
(1.007)

4.7 g of 1-(3-trifluoromethylphenoxy)-butan-2-ol and 2.7 g of benzyl isocyanate are dissolved in 60 ml of ethyl acetate. After addition of one drop of triethylamine, the reaction mixture is allowed to stand for 20 hours at 22° C. The solvent is stripped off and the residue is stirred in n-hexane. The desired crystalline product, O—[1-(3-trifluoromethylphenoxy)-2-butyl]-N-benzylcarbamate, is obtained in a yield of 5.2 g; m.p. 73°–74° C.

The compounds of formula I listed in the following Table 1 are prepared in analogous manner:

TABLE 1

Compounds of formula I

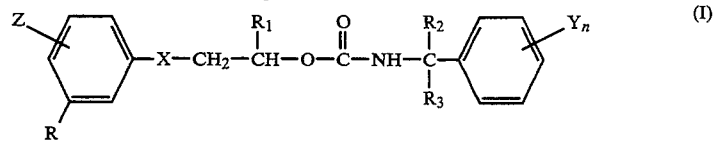
(I)

| Cmpd. No. | R | Z | X | n | Y | $R_1$ | $R_2$ | $R_3$ | Physical data |
|---|---|---|---|---|---|---|---|---|---|
| 1.1 | $CF_3$ | H | O | 0 | — | $CH_3$ | H | H | m.p. 71–74° C. |
| 1.2 | $CF_3$ | H | O | 1 | 2-F | $CH_3$ | H | H | |
| 1.3 | $CF_3$ | H | O | 1 | 2-Cl | $CH_3$ | H | H | |
| 1.4 | $CF_3$ | H | O | 1 | 2-$CH_3$ | $CH_3$ | H | H | |
| 1.5 | $CF_3$ | H | O | 1 | 3-Cl | $CH_3$ | H | H | |
| 1.6 | $CF_3$ | H | O | 1 | 3-F | $CH_3$ | H | H | |
| 1.7 | $CF_3$ | H | O | 0 | — | $C_2H_5$ | H | H | m.p. 73–74° C. |
| 1.8 | $CF_3$ | H | O | 1 | 2-F | $C_2H_5$ | H | H | m.p. 43–47° C. |
| 1.9 | $CF_3$ | H | O | 1 | 2-Cl | $C_2H_5$ | H | H | wax |
| 1.10 | $CF_3$ | H | O | 1 | 2-$CH_3$ | $C_2H_5$ | H | H | m.p. 61–63° C. |
| 1.11 | $CF_3$ | H | O | 1 | 3-Cl | $C_2H_5$ | H | H | $n_D^{22} = 1.5125$ |
| 1.12 | $CF_3$ | H | O | 1 | 3-$CH_3$ | $C_2H_5$ | H | H | mp. 62–64° C. |
| 1.13 | $CF_3$ | H | O | 1 | 3-F | $C_2H_5$ | H | H | |
| 1.14 | $CF_3$ | H | O | 1 | 4-F | $C_2H_5$ | H | H | m.p. 63–65° C. |
| 1.15 | $CF_3$ | H | O | 1 | 4-Cl | $C_2H_5$ | H | H | wax |
| 1.16 | $CF_3$ | H | O | 1 | 4-$CH_3$ | $C_2H_5$ | H | H | m.p. 82–85° C. |
| 1.17 | $CF_3$ | H | O | 1 | 2-$OCH_3$ | $C_2H_5$ | H | H | m.p. 80–82° C. |
| 1.18 | $CF_3$ | H | O | 1 | 3-$OCH_3$ | $C_2H_5$ | H | H | $n_D^{22} = 1.5079$ |
| 1.19 | $CF_3$ | H | O | 1 | 4-$OCH_3$ | $C_2H_5$ | H | H | $n_D^{22} = 1.5090$ |
| 1.20 | $CF_3$ | H | O | 1 | 2-$CF_3$ | $C_2H_5$ | H | H | m.p. 63–64° C. |
| 1.21 | $CF_3$ | H | O | 1 | 3-$CF_3$ | $C_2H_5$ | H | H | m.p. 44–46° C. |
| 1.22 | $CF_3$ | H | O | 1 | 2-CN | $C_2H_5$ | H | H | |
| 1.23 | $CF_3$ | H | O | 2 | 2,6-F | $C_2H_5$ | H | H | $n_D^{22} = 1.4915$ |
| 1.24 | $CF_3$ | H | O | 2 | 2,4-F | $C_2H_5$ | H | H | m.p. 77–79° C. |
| 1.25 | Cl | H | O | 0 | — | $C_2H_5$ | H | H | m.p. 55–58° C. |
| 1.26 | Cl | H | O | 0 | — | $CH_3$ | H | H | |
| 1.27 | Cl | H | O | 1 | 2-F | $C_2H_5$ | H | H | |
| 1.28 | Cl | H | O | 1 | 2-$CH_3$ | $C_2H_5$ | H | H | |
| 1.29 | $NO_2$ | H | O | 0 | — | $C_2H_5$ | H | H | m.p. 70–72° C. |
| 1.30 | $NO_2$ | H | O | 1 | 2-F | $C_2H_5$ | H | H | |
| 1.31 | $NO_2$ | H | O | 1 | 2-Cl | $C_2H_5$ | H | H | |
| 1.32 | CN | H | O | 0 | — | $C_2H_5$ | H | H | m.p. 79–82° C. |
| 1.33 | CN | H | O | 1 | 2-$CH_3$ | $C_2H_5$ | H | H | |
| 1.34 | CN | H | O | 2 | 2,3-Cl | $C_2H_5$ | H | H | |
| 1.35 | CN | H | O | 0 | — | $C_2H_5$ | $C_2H_5$ | H | |
| 1.36 | $CF_3$ | H | O | 0 | — | $C_2H_5$ | $CH_3$ | H | $n_D^{22} = 1.5005$ |
| 1.37 | $CF_3$ | H | O | 0 | — | $C_2H_5$ | $CH_3$ | $CH_3$ | |
| 1.38 | $CF_3$ | H | O | 0 | — | $C_2H_5$ | $CH_3$ | $C_2H_5$ | |
| 1.39 | $CF_3$ | H | O | 0 | — | $C_2H_5$ | $C_2H_5$ | $C_2H_5$ | |
| 1.40 | $CF_3$ | H | O | 0 | — | $CH_3$ | $C_2H_5$ | H | |
| 1.41 | $CF_3$ | H | S | 0 | — | $C_2H_5$ | H | H | $n_D^{25}$ 1.5325 |
| 1.42 | $CF_3$ | H | S | 1 | 2-F | $C_2H_5$ | H | H | |
| 1.43 | $CF_3$ | H | S | 1 | 2-Cl | $C_2H_5$ | H | H | |
| 1.44 | $CF_3$ | H | SO | 0 | — | $C_2H_5$ | H | H | |
| 1.45 | $CF_3$ | H | $SO_2$ | 0 | — | $C_2H_5$ | H | H | |
| 1.46 | $CF_3$ | H | O | 0 | — | i-$C_3H_7$ | H | H | $n_D^{25}$ 1.5094 |
| 1.47 | $CF_3$ | H | O | 1 | 2-F | i-$C_3H_7$ | H | H | |
| 1.48 | $CF_3$ | H | O | 0 | — | n-$C_3H_7$ | H | H | |
| 1.49 | $CF_3$ | H | O | 0 | — | i-$C_4H_9$ | H | H | m.p. 53–55° C. |

TABLE 1-continued

Compounds of formula I $$Z \underset{R}{\overset{}{\diagdown}} -X-CH_2-\underset{R_1}{\overset{}{C}}H-O-\overset{O}{\overset{\|}{C}}-NH-\underset{R_3}{\overset{R_2}{C}}-\diagup Y_n \quad (I)$$

| Cmpd. No. | R | Z | X | n | Y | $R_1$ | $R_2$ | $R_3$ | Physical data |
|---|---|---|---|---|---|---|---|---|---|
| 1.50 | $CF_3$ | H | O | 0 | — | $s$-$C_4H_9$ | H | H | |
| 1.51 | $CF_3$ | H | O | 0 | — | $n$-$C_4H_9$ | H | H | $n_D^{22}$ 1.5012 |
| 1.52 | $CF_3$ | H | O | 0 | — | $n$-$C_5H_{11}$ | H | H | |
| 1.53 | $CF_3$ | H | O | 0 | — | $s$-$C_5H_{11}$ | H | H | |
| 1.54 | $CF_3$ | 4-F | O | 0 | — | $C_2H_5$ | H | H | |
| 1.55 | $CF_3$ | 2-F | O | 0 | — | $C_2H_5$ | H | H | |
| 1.56 | $OCF_3$ | H | O | 0 | — | $C_2H_5$ | H | H | m.p. 45-46°C |
| 1.57 | $OCF_3$ | H | O | 1 | 2-$CH_3$ | $C_2H_5$ | H | H | |
| 1.58 | $OCF_3$ | H | O | 1 | 2-F | $C_2H_5$ | H | H | |
| 1.59 | Br | H | O | 0 | — | $C_2H_5$ | H | H | |
| 1.60 | $OCHF_2$ | H | O | 0 | — | $C_2H_5$ | H | H | |
| 1.61 | 2,3-$OCF_2O$— | | O | 0 | — | $CH_3$ | H | H | |
| 1.62 | 2,3-$OCF_2O$— | | O | 0 | — | $C_2H_5$ | H | H | m.p. 65-67°C |
| 1.63 | 2,3-$OCF_2O$— | | O | 1 | 2-F | $C_2H_5$ | H | H | |
| 1.64 | 2,3-$OCF_2O$— | | O | 1 | 2-$CH_3$ | $C_2H_5$ | H | H | viscous oil |
| 1.65 | 2,3-$OCF_2O$— | | O | 1 | 3-$CF_3$ | $C_2H_5$ | H | H | |
| 1.66 | 2,3-$OCF_2O$— | | O | 1 | 2-Cl | $C_2H_5$ | H | H | |
| 1.67 | 2,3-$OCF_2O$— | | O | 1 | 3-Cl | $C_2H_5$ | H | H | |
| 1.68 | 2,3-$OCF_2O$— | | O | 0 | — | $C_2H_5$ | $C_2H_5$ | H | |
| 1.69 | 2,3-$OCF_2O$— | | S | 0 | — | $C_2H_5$ | H | H | |
| 1.70 | 2,3-$OCF_2O$— | | $SO_2$ | 0 | — | $C_2H_5$ | H | H | |
| 1.71 | 2,3-$OCF_2O$— | | O | 2 | 2-$CH_3$, 4-F | $C_2H_5$ | H | H | $n_D^{25}$ 1.5047 |
| 1.72 | 2,3-$OCF_2O$— | | O | 2 | 2Cl,4F | $C_2H_5$ | H | H | m.p. 72-74° C. |
| 1.73 | 2,3-$OCF_2O$— | | O | 1 | 2-$CF_3$ | $C_2H_5$ | H | H | m.p. 70-71° C. |
| 1.74 | $CF_3$ | H | O | 0 | — | $CH_3$ | $CH_3$ | H | diaster. A, m.p. 107-108° C. |
| 1.75 | $CF_3$ | H | O | 0 | — | $CH_3$ | $CH_3$ | H | diaster. B, wax |
| 1.76 | $CF_3$ | H | O | 1 | 4-Cl | $C_2H_5$ | $CH_3$ | $CH_3$ | $n_D^{23}$ 1.5031 |
| 1.77 | $CF_3$ | H | O | 2 | 2,4-Cl | $C_2H_5$ | H | H | $n_D^{22}$ 1.5224 |
| 1.78 | $CF_3$ | H | O | 2 | 3,4-Cl | $C_2H_5$ | H | H | m.p. 69-72° C. |
| 1.79 | $CF_3$ | H | O | 2 | 2,5-F | $C_2H_5$ | H | H | m.p. 54-56° C. |
| 1.80 | $CF_3$ | H | O | 2 | 3,4-F | $C_2H_5$ | H | H | m.p. 62-64° C. |
| 1.81 | $CF_3$ | H | O | 1 | 2-Br | $C_2H_5$ | H | H | m.p. 63-65° C. |
| 1.82 | $CF_3$ | H | O | 2 | 2-$CH_3$, 6-Cl | $C_2H_5$ | H | H | m.p. 58-60° C. |
| 1.83 | $CF_3$ | H | O | 2 | 2-$CH_3$, 6-$C_2H_5$ | $C_2H_5$ | H | H | oil |
| 1.84 | $CF_3$ | H | O | 2 | 2,6$CH_3$ | $C_2H_5$ | H | H | m.p. 72-73° C. |
| 1.85 | $CF_3$ | H | O | 2 | 2-$CH_3$, 5-F | $C_2H_5$ | H | H | m.p. 73-74° C. |
| 1.86 | $CF_3$ | H | O | 2 | 2,3$CH_3$ | $C_2H_5$ | H | H | m.p. 73-74° C. |
| 1.87 | $CF_3$ | H | O | 2 | 2-$CH_3$, 4-F | $C_2H_5$ | H | H | m.p. 60-61° C. |
| 1.88 | $CF_3$ | H | O | 2 | 2Cl,4F | $C_2H_5$ | H | H | m.p. 68-70° C. |

C. Biological Examples

Example B1 Pre-emergence herbicidal action

Monocot and dicot test plants are sown in plastic pots in standard soil. Immediately after sowing, an aqueous suspension of the test compound prepared from a 25% wettable powder (Example F1) is sprayed on to the plants in a concentration of 2 kg a.i./ha (500 l of water/ha). The test plants are then cultivated in a greenhouse under optimum conditions. The test is evaluated after 3 weeks on a rating scale from 1 to 9 (1=total damage, 9=no action). Ratings from 1 to 4 (especially from 1 to 3) denote good to very good herbicidal action. The same result is obtained with a wettable powder concentrate (Example F3), dispersible granulate (Example F4), emulsifiable concentrate (Example F2) and suspension concentrate (Example F6).

Test plants: Avena, Setaria, Sinapsis, Stellaria.

In this test the compounds of formula I according to the Examples in Table 1 exhibit strong herbicidal action.

Examples of the good herbicidal action of the compounds of formula I are shown in Table B1:

TABLE B1

| Cmpd. No. | Conc. [kg ai/ha] | Preemergence action | | | |
|---|---|---|---|---|---|
| | | Avena | Setaria | Sinapis | Stellaria |
| 1.007 | 2 | 3 | 1 | 1 | 1 |
| 1.009 | 2 | 7 | 1 | 1 | 1 |
| 1.010 | 2 | 6 | 1 | 1 | 1 |
| 1.036 | 2 | 8 | 4 | 3 | 3 |

EIxample 2 Post-emergence herbicidal action (contact herbicide)

Monocot and dicot plants are cultivated in a greenhouse in plastic pots with standard soil and sprayed in the 4- to 6-leaf stage with an aqueous suspension prepared from a 25% wettable powder (Example F1) of the test compound in a concentration of 2 kg a.i./ha (500 l of water/ha). The test plants are then cultivated in a greenhouse under optimum conditions. The test is evaluated after 3 weeks on a a rating scale from 1 to 9 (1=total damage, 9=no action). Ratings from 1 to 4 (especially from 1 to 3) deonote good to very good herbicidal action. The same result is obtained with a wettable powder concentrate (Example F3), dispersible granulate (Example F4), emulsifiable concentrate (Example F2) and suspension concentrate (Example F6).

Test plants: Avena, Setaria, Sinapsis, Stellaria.

In this test also the compounds of formula I according to the Examples in Table 1 exhibit strong herbicidal action.

Examples of the good herbicidal action of the compounds of formula I are shown in Table B2:

TABLE 2

| Cmpd. No. | Conc. [kg ai/ha] | Post-emergence action | | | |
|---|---|---|---|---|---|
| | | Avena | Setaria | Sinapis | Stellaria |
| 1.007 | 2 | 6 | 5 | 2 | 3 |
| 1.009 | 2 | 7 | 4 | 2 | 4 |
| 1.010 | 2 | 7 | 4 | 2 | 4 |
| 1.036 | 2 | 8 | 5 | 2 | 6 |

What is claimed is:

1. A compound of formula I

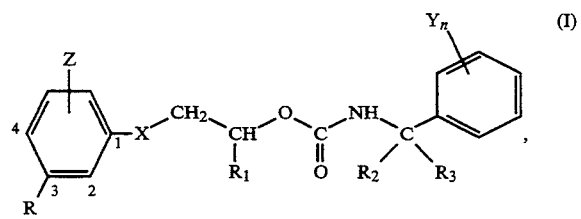

wherein
Z and R together in 2- and 3-position of the phenyl ring form the group —OCF$_2$O—;
R$_1$ is C$_1$–C$_5$alkyl;
R$_2$ and R$_3$ are each independently of the other hydrogen, methyl or ethyl;
X is oxygen, sulfur, —SO— or —SO$_2$—;
Y is hydrogen, halogen, C$_1$–C$_3$alkyl, C$_1$–C$_3$haloalkyl, C$_1$–C$_3$alkoxy or cyano; and
N is 0, 1 or 2;
or a diastereoisomer thereof.

2. A compound according to claim 1, wherein R$_1$ is methyl or ethyl.

3. A compound according to claim 1, wherein R$_2$ and R$_3$ are each independently of the other hydrogen or methyl.

4. A compound according to claim 1, wherein X is oxygen or sulfur.

5. A compound according to claim 1, wherein Y is hydrogen, fluoro, chloro, methyl, trifluoromethyl, methoxy or cyano.

6. A compound according to claim 1, wherein R$_1$ is ethyl; R$_2$ and R$_3$ are hydrogen; X is oxygen; Y is fluoro, chloro, methyl, trifluoromethyl, methoxy or cyano; and n is 0 or 1.

7. A compound according to claim 1, wherein Y is fluoro, chloro, methyl, trifluoromethyl, methoxy or cyano.

8. A compound according to claim 7, wherein R$_1$ is methyl or ethyl; R$_2$ is hydrogen or methyl; R$_3$ is hydrogen; X is oxygen; and Y is fluoro, chloro, methyl or methoxy.

9. A compound according to claim 1 of formula Ib

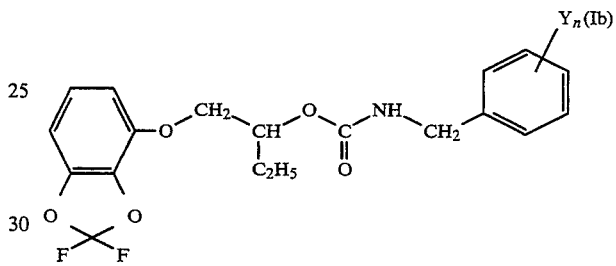

wherein Y and n are as defined in claim 1.

10. A compound according to claim 9, wherein Y is fluoro, chloro, methyl or methoxy.

11. A herbicidal composition which comprises a compound of formula I as claimed in claim 1.

12. A composition according to claim 11, which comprises from 0.1 to 95% by weight of a compound of formula I, 1 to 99% of a solid or liquid carrier, and 0 to 25% of a surfactant.

13. A method of controlling undesirable plant growth, which comprises treating the plants or the locus thereof with a herbicidally effective amount of a compound of formula I as claimed in claim 1 or of a composition containing such a compound.

14. A method according to claim 13, wherein a compound of formula I is applied in a concentration of 0.005 to 2 Kg/ha.

15. A method according to claim 13 of selectively controlling weeds pre- or postemergence in crops of useful plants.

* * * * *